United States Patent
Sakuma et al.

(10) Patent No.: US 8,278,907 B2
(45) Date of Patent: Oct. 2, 2012

(54) PARTICULATE MATTER DETECTION DEVICE AND METHOD FOR MANUFACTURING THE SAME

(75) Inventors: Takeshi Sakuma, Nagoya (JP); Atsuo Kondo, Okazaki (JP); Takashi Egami, Aichi-prefecture (JP)

(73) Assignee: NGK Insulators, Ltd., Nagoya (JP)

( * ) Notice: Subject to any disclaimer, the term of this patent is extended or adjusted under 35 U.S.C. 154(b) by 500 days.

(21) Appl. No.: 12/559,762

(22) Filed: Sep. 15, 2009

(65) Prior Publication Data

US 2010/0071441 A1    Mar. 25, 2010

(30) Foreign Application Priority Data

Sep. 25, 2008 (JP) ................ 2008-246461

(51) Int. Cl.
*G01N 27/00* (2006.01)
(52) U.S. Cl. .............. 324/71.4; 73/23.33; 73/28.01
(58) Field of Classification Search .......... None
See application file for complete search history.

(56) References Cited

U.S. PATENT DOCUMENTS

| | | | | |
|---|---|---|---|---|
| 3,628,139 A | * | 12/1971 | Huber | 377/12 |
| 3,784,902 A | * | 1/1974 | Huber | 324/464 |
| 4,939,466 A | * | 7/1990 | Johnson et al. | 324/464 |

FOREIGN PATENT DOCUMENTS

JP    60-123761 A1    7/1985

* cited by examiner

*Primary Examiner* — Vinh Nguyen
(74) *Attorney, Agent, or Firm* — Burr & Brown

(57) ABSTRACT

A particulate matter detection device including a detection device main body which has one end provided with a through hole a pair of electrodes embedded in a wall through which the through hole is formed, and covered with a dielectric material; wires extending from the electrodes to the other end of the main body; and a ground electrode provided at a position sandwiched between the wires. The device can electrically adsorb, on the wall surface of the through hole, a charged particle in a fluid flowing into the through hole, or a particle charged by electric discharge caused in the through hole by applying a voltage across the pair of electrodes. The device can measure the changes of the electric properties of the wall through which the through hole is formed, thereby detecting particles adsorbed on the wall surface of the through hole.

17 Claims, 4 Drawing Sheets

PARTICULATE MATTER DETECTION DEVICE AND METHOD FOR MANUFACTURING THE SAME

FIELD OF THE INVENTION

The present invention relates to a particulate matter detection device. More particularly, it relates to a particulate matter detection device which is small-sized, can minimize measurement errors and can inexpensively be manufactured.

BACKGROUND OF THE INVENTION

A flue exhaust gas or a diesel engine exhaust gas includes a particulate matter (PM) such as soot, which has been a cause for air pollution. To remove the PM, a filter made of a ceramic material or the like (a diesel particulate filter: DPF) is broadly used. The ceramic DPF can be used for a long period of time, but a defect such as cracking or melting due to heat deterioration or the like occurs at times, and the PM might leak though a leak amount is small. When such a defect occurs, it is remarkably important from the viewpoint of the prevention of the air pollution to immediately detect the occurrence of the defect and to recognize the abnormality of a device.

As a method of detecting the occurrence of such a defect, there is a method of providing a particulate matter detection device on the downstream side of the DPF (e.g., see JP-A-60-123761).

SUMMARY OF THE INVENTION

In the invention disclosed in JP-A-60-123761, a particulate matter is charged by corona discharge, and the ion current of the particulate matter is measured to determine the amount thereof. Thus, in the method of charging the particulate matter to measure the ion current thereof, the ion current to charge the particulate matter is weak, and hence there is a problem that a large-scaled detection circuit is required for detecting the weak ion current, which increases cost. Moreover, when an exhaust gas has a high flow rate, the particulate matter cannot effectively be charged, and hence there is a problem that the measured amount of the particulate matter is smaller than the amount of the particulate matter actually contained in the exhaust gas, which error is large.

The present invention has been developed in view of the above problem, and an object thereof is to provide a particulate matter detection device which is small-sized, can minimize measurement errors and can inexpensively be manufactured.

To achieve the above object, the present invention provides the following particulate matter detection device.

According to a first aspect of the present invention, a particulate matter detection device is provided, comprising: a detection device main body which has one end provided with at least one through hole and which is prolonged in one direction; at least a pair of electrodes embedded in a wall through which the through hole is formed, and covered with a dielectric material; wires extending from the pair of electrodes respectively to the other end of the detection device main body; and a strip-like ground electrode provided at a position sandwiched between the wires extending from the pair of electrodes respectively, the particulate matter detection device being configured to electrically adsorb, on the wall surface of the through hole, a charged particulate matter contained in a fluid flowing into the through hole, or a particulate matter which is charged by electric discharge caused in the through hole by applying a voltage across the pair of electrodes and which is contained in the fluid flowing into the through hole, and being configured to measure the changes of the electric properties of the wall through which the through hole is formed, thereby detecting the particulate matter adsorbed on the wall surface of the through hole.

According to a second aspect of the present invention, the particulate matter detection device according to the first aspect is provided, wherein the detection device main body has the other end provided with a takeout terminal of at least one of the pair of electrodes.

According to a third aspect of the present invention, the particulate matter detection device according to the first or second aspects is provided, wherein the ground electrode is disposed in a plane parallel to both the longitudinal direction and the width direction of the detection device main body, the width of the ground electrode is 70 to 95% of that of the detection device main body, and the length of the ground electrode is 50 to 95% of that of the detection device main body.

According to a fourth aspect of the present invention, the particulate matter detection device according to any one of the first to third aspects is provided, further comprising: a heating section for temperature control provided in the detection device main body so as to extend along the wall surface of the through hole, and configured to stably measure the changes of the electric properties of the wall through which the through hole is formed, the detection device main body having the other end being provided with a takeout terminal of the heating section.

According to a fifth aspect of the present invention, the particulate matter detection device according to any one of the first to fourth aspects is provided, wherein at least one of an inlet portion of the through hole into which the fluid flows and an outlet portion of the through hole from which the fluid is discharged is enlarged.

According to a sixth aspect of the resent invention, the particulate matter detection device according to any one of the first to fifth aspects is provided, wherein the sectional shape of the detection device main body crossing the central axis thereof at right angles gradually thickens from the one end of the detection device main body to the center thereof, thickens most at the center thereof, and further gradually becomes thin toward the other end thereof in the extending direction of the through hole.

According to a seventh aspect of the present invention the particulate matter detection device according to any one of the first to sixth aspects is provided, which is configured to apply the voltage across the pair of electrodes to cause the electric discharge in the through hole, thereby oxidizing and removing the particulate matter adsorbed on the wall surface of the through hole.

According to an eighth aspect of the present invention, the particulate matter detection device according to any one of the first to seventh aspects is provided, wherein the electric discharge caused in the through hole is one type selected from the group consisting of silent discharge, streamer discharge, and corona discharge.

According to a ninth aspect of the present invention, the particulate matter detection device according to any one of the first to eighth aspects is provided, wherein the dielectric material is at least one selected from the group consisting of alumina, cordierite, mullite, glass, zirconia, magnesia, and titania.

According to a tenth aspect of the present invention, a method for manufacturing a particulate matter detection device is provided, the method comprising the steps of: forming a forming material containing a ceramic material into a tape-like shape to prepare a plurality of green sheets which are prolonged in one direction; providing an electrode in one end of one surface of each of the two green sheets and providing wires extending from the electrodes to the other end thereof, to form the green sheets provided with the electrodes; providing a ground electrode at a position where the one green sheet is superimposed on the wires when the green sheet is superimposed on the green sheets provided with the electrodes, to form the green sheet provided with the ground electrode; forming a cut portion which becomes a through hole at a position where the one green sheet is superimposed on the electrode when the green sheet is superimposed on the green sheets provided with the electrodes, to form the green sheet provided with the cut portion; superimposing the plurality of green sheets on the two green sheets provided with the electrodes, respectively, to form the green sheets in which the electrodes are embedded in a state in which the electrodes and the wires are covered with the green sheets; laminating the plurality of green sheets so that the green sheet provided with the ground electrode and the green sheet provided with the cut portion are sandwiched between the two green sheets in which the electrodes are embedded, to form a green sheet laminate having a state in which the cut portion is sandwiched between the two electrodes and in which the ground electrode is sandwiched between the two wires; and drying and firing the green sheet laminate to obtain the particulate matter detection device.

According to the particulate matter detection device of the present invention, at least the pair of electrodes are embedded in the wall of the detection device main body through which the through hole is formed, and the voltage is applied across the pair of electrodes to cause the electric discharge in the through hole, whereby the device can charge the particulate matter present in the through hole by the electric discharge, and can electrically adsorb the charged particulate matter by the electrodes. Therefore, in the exhaust gas flowing on the downstream side of a DPF, the mass of the particulate matter only of the exhaust gas which has flowed into the through hole can be measured. In consequence, all the particulate matter contained in the exhaust gas flowing on the downstream side of the DPF is not directly measured, but the mass of only the particulate matter flowing into the through hole can be measured to estimate the amount of the particulate matter contained in the whole exhaust gas. Consequently, the particulate matter detection device can be miniaturized, and accordingly can be installed in a small space. Furthermore, the device can inexpensively be manufactured. Moreover, even when the whole flow rate of the exhaust gas flowing on the downstream side of the DPF is high, only part of the exhaust gas (the particulate matter) is introduced into the through hole, so that all the particulate matter in the through hole can effectively be charged, and a measured value with a reduced error can be obtained. Moreover, the detection device main body is formed so as to be prolonged in one direction, and has one end provided with the through hole in which at least the pair of electrodes are provided (embedded). Therefore, only a portion of the main body including the through hole and the pair of electrodes is inserted into a pipe through which the high-temperature exhaust gas circulates, and the other end of the main body can be protruded externally from the pipe. In consequence, portions such as the takeout terminals of the pair of electrodes which are preferably not exposed to the high temperature can be protruded externally from the pipe, and hence the particulate matter can accurately and stably be detected. Furthermore, the strip-like ground electrode is disposed at the position sandwiched between the wires extending from the pair of electrodes to the other end of the detection device main body, so that electric properties across the pair of electrodes can be detected while suppressing the influences of the wires extending from the pair of electrodes, respectively. In consequence, the changes of the electric properties of the wall through which the through hole is formed can accurately be measured.

Moreover, according to the present invention, the method for manufacturing the particulate matter detection device includes the steps of forming the forming material containing the ceramic material into the tape-like shape to prepare the plurality of green sheets which are prolonged in one direction; processing a part of the obtained plurality of green sheets into the predetermined green sheets provided with the electrodes, the predetermined green sheet provided with the ground electrode, and the predetermined green sheet provided with the cut portion; superimposing the plurality of green sheets on the two green sheets provided with the electrodes, respectively, to form the green sheets in which the electrodes are embedded in a state in which the electrodes and the wires are covered with the green sheets; laminating the green sheets so that the green sheet provided with the ground electrode and the green sheet provided with the cut portion are sandwiched between the two green sheets in which the electrodes are embedded, to form the green sheet laminate having the state in which the cut portion is sandwiched between the two electrodes and in which the ground electrode is sandwiched between the two wires; and drying and firing the green sheet laminate to obtain the particulate matter detection device. Therefore, the particulate matter detection device of the present invention can efficiently be obtained.

DESCRIPTION OF REFERENCE NUMERALS

1: detection device main body, 1*a*: one end, 1*b*: other end, 1*c*: one tip portion, 1*d*: other tip portion, 2: through hole, 2*a*: inlet portion, 2*b*: enlarged portion, 11, 12: electrode, 11*a*, 12*a*, 13*a* and 14*a*: takeout terminal, 11*b*, 12*b*, 13*b* and 14*b*: wires, 14: ground electrode, 13: heating section, 100, 200 and 300: particulate matter detection device, W1: enlarged width, W2: non-enlarged width, L1: depth of enlarged portion, and L2: length of through hole in gas circulating direction.

DETAILED DESCRIPTION OF THE INVENTION

Next, embodiments of the present invention will be described in detail with reference to the drawings, but it should be understood that the present invention is not limited to the following embodiments and is appropriately altered or improved in design or the like based on the ordinary knowledge of a person with ordinary skill without departing from the scope of the present invention.

Figure 1A:
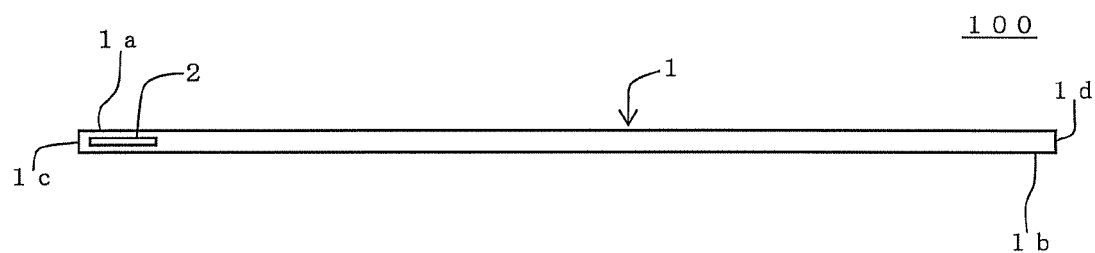
FIG. 1A is a front view schematically showing one embodiment of a particulate matter detection device of the present invention.
Figure 1B:
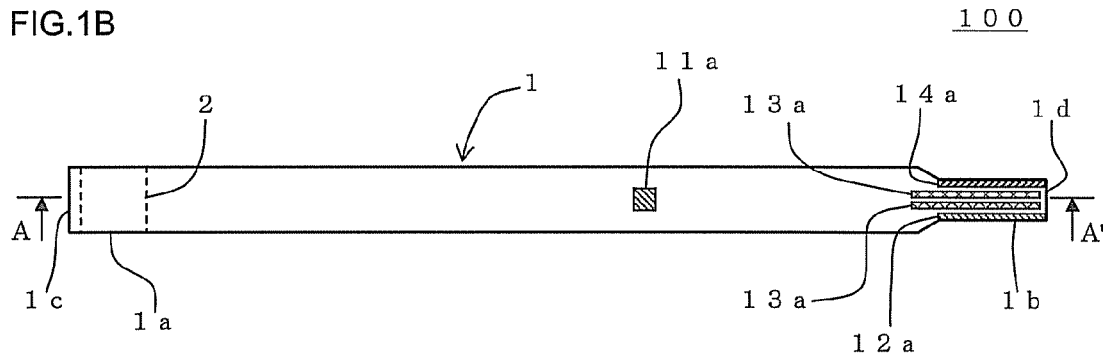
FIG. 1B is a side view schematically showing the embodiment of the particulate matter detection device of the present invention.
Figure 2:
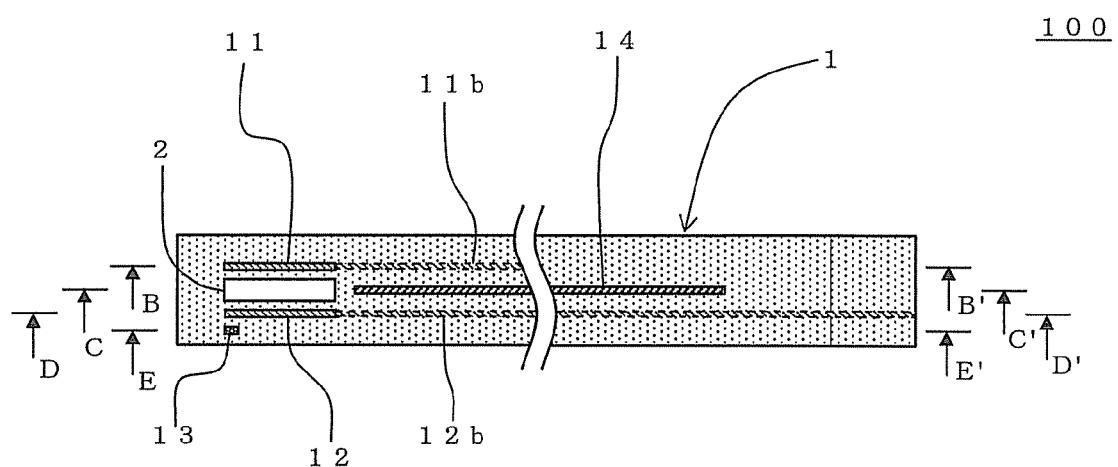
FIG. 2 is a schematic diagram showing a section cut along the A-A' line of FIG. 1B.

FIG. 1A is a front view schematically showing one embodiment of a particulate matter detection device of the present invention, FIG. 1B is a side view schematically showing the embodiment of the particulate matter detection device of the present invention, and FIG. 2 is a schematic diagram showing a section cut along the A-A' line of FIG. 1B. It is to be noted that in FIG. 1A, a takeout terminal (a takeout terminal 12*a* or the like) is omitted. As shown in FIGS. 1A, 1B and 2, a particulate matter detection device 100 of the present embodiment includes a detection device main body 1 which has one end 1*a* provided with a through hole (a cavity) 2 and which is prolonged in one direction, and a pair of electrodes 11, 12 provided (embedded) in a wall through which the through hole 2 is formed, and covered with a dielectric material. Here, at least one through hole 2 needs to be formed, however, two or more holes may be formed. Moreover, at least the pair of electrodes need to be disposed, and two or more pairs thereof may be disposed. In the particulate matter detection device 100 of the present embodiment, the pair of electrodes 11, 12 are embedded in the detection device main body 1, and the detection device main body 1 is made of the dielectric material, whereby the pair of electrodes 11, 12 are covered with the dielectric material, respectively. Moreover, in the particulate matter detection device 100 of the present embodiment, a charged particulate matter contained in a fluid flowing into the through hole 2 or a particulate matter charged by electric discharge caused in the through hole 2 by applying a voltage across the pair of electrodes 11, 12 contained in the fluid flowing into the through hole 2, can electrically be adsorbed on the wall surface of the through hole 2. Furthermore, the changes of the electric properties of the wall through which the through hole 2 is formed can be measured to detect the mass of the particulate matter adsorbed on the wall surface of the through hole 2. In consequence, the particulate matter detection device 100 of the present embodiment can pass an exhaust gas or the like through the through hole 2 to detect the particulate matter contained in the exhaust gas.

Consequently, in the exhaust gas flowing on the downstream side of a DPF, the mass of the particulate matter only of the exhaust gas flowing into the through hole can be measured, all the particulate matter contained in the exhaust gas flowing on the downstream side of the DPF is not directly measured, but the mass of the only particulate matter flowing into the through hole can be measured to estimate the amount of the particulate matter contained in the whole exhaust gas. In consequence, the particulate matter detection device can be miniaturized, and accordingly can be installed in a small space. Furthermore, the device can inexpensively be manufactured. Moreover, even when the whole flow rate of the exhaust gas flowing on the downstream side of the DPF is high, an only part of the exhaust gas (the particulate matter) is introduced into the through hole, so that all the particulate matter in the through hole can effectively be charged, and a measured value with a less error can be obtained. Moreover, the detection device main body is formed so as to be prolonged in one direction, and has one end provided with the through hole, and at least the pair of electrodes are provided (embedded). Therefore, a portion of the main body including the through hole and the pair of electrodes is only inserted into a pipe through which the high-temperature exhaust gas circulates, and the other end of the main body can be protruded externally from the pipe. In consequence, portions such as the takeout terminals of the pair of electrodes which are preferably not exposed to the high temperature can be protruded externally from the pipe, and hence the particulate matter can accurately and stably be detected.

Furthermore, in the particulate matter detection device of the present embodiment, the strip-like ground electrode is disposed at the position sandwiched between the wires extending from the pair of electrodes respectively to the other end of the detection device main body. The ground electrode is a grounded electrode. The particulate matter detection device of the present embodiment can detect predetermined electric properties across the pair of electrodes to measure the changes of the electric properties of the wall through which the through hole is formed, thereby detecting the particulate matter adsorbed on the wall surface of the through hole. However, when the predetermined electric properties across the pair of electrodes are detected, the predetermined electric properties across the two wires connected to the pair of electrodes and embedded in the dielectric material are also detected. That is, the obtained measured value is a value detected by both the pair of electrodes and the two wires. When the predetermined electric properties across the two wires have a large influence, the electric properties of the wall through which the through hole is formed change. Even in a case where the changes of the electric properties of the wall through which the through hole is formed are detected by the pair of electrodes, the changes of the electric properties of the wall through which the through hole is formed cannot accurately be measured, because the electric properties across the two wires connected to the pair of electrodes are simultaneously measured. The particulate matter detection device of the present embodiment can detect the electric properties across the pair of electrodes while suppressing the influences of the wires extending from the pair of electrodes, respectively, by the ground electrode, which can solve the problem of measurement error due to the influences of the wires. In consequence, the changes of the electric properties of the wall through which the through hole is formed can accurately be measured.

When any ground electrode is not disposed and the voltage is applied across the pair of electrodes, a current flows from the one wire connected to one of the pair of electrodes to the other wire connected to the other electrode through the dielectric material sandwiched between the two wires, whereby the electric properties across the two wires are detected. On the other hand, in the particulate matter detection device of the present embodiment in which the ground electrode is disposed between the two wires, the current flows from the one wire to the ground electrode, and the current does not flow from the one wire to the other wire. Therefore, the electric properties across the one wire and the other wire are not detected. In a case where the voltage is applied across the pair of electrodes, only the electric properties of the wall through which the through hole is positioned between the pair of electrodes can be detected.

In the particulate matter detection device 100 of the present embodiment, the other end 1b of the detection device main body 1 is preferably provided with a takeout terminal of at least one of the pair of electrodes 11, 12. The takeout terminal is a portion electrically connected to each electrode disposed in the detection device main body 1 of the particulate matter detection device 100 and connected to a wire from a power source or the like for applying the voltage from the outside to the electrode. The particulate matter detection device 100 has a plurality of takeout terminals (takeout terminals 11a, 12a, 13a and 14a) independently connected to the pair of electrodes 11, 12, a heating section 13, a ground electrode 14 and the like, respectively. In the particulate matter detection device 100 of the present embodiment shown in FIG. 1B, the takeout terminal 12a of the electrode 12 is disposed in the other end 1b of the detection device main body 1. Thus, the takeout terminal of at least one of the pair of electrodes 11, 12 can be disposed in the other end 1b of the detection device main body 1 to increase a space between the portion provided with the through hole and the pair of electrodes (the one end 1a) and the takeout terminal. Therefore, the only one end 1a provided with the through hole and the like can be inserted into a pipe through which a high-temperature exhaust gas circulates, and the other end 1b provided with the takeout terminal 12a can be protruded externally from the pipe. When the temperature of the takeout terminal 12a is raised, the detection accuracy of the particulate matter lowers, and the particulate matter cannot easily be detected stably at times. Alternatively, when the device is used for a long period of time, a contact defect between an electric terminal and a harness to be connected to the outside occurs, and the measurement cannot be performed. To solve the problem, the takeout terminal 12a is protruded externally from the pipe, and is not exposed to the high temperature, whereby the particulate matter can accurately and stably be detected.

As shown in FIG. 1B, the takeout terminal 12a in the other end 1b of the detection device main body 1 is preferably disposed in the side surface of the other end 1b of the detection device main body 1 so as to extend in a longitudinal direction. Moreover, the takeout terminal 12a is preferably disposed in the one end of the side surface of the other end 1b of the detection device main body 1 in a width direction thereof. Furthermore, in FIG. 1B, the other end 1b of the detection device main body 1 has a decreased width, but the width of the other end 1b may be decreased in this manner or may not be decreased. There is not any special restriction on the shape and size of the takeout terminal 12a. The takeout terminal preferably has, for example, a strip-like shape with a width of 0.1 to 2.0 mm and a length of 0.5 to 20 mm. Examples of the material of the takeout terminal 12a include Ni, Pt, Cr, W, Mo, Al, Au, Ag and Cu.

Both the takeout terminals of the pair of electrodes 11, 12 may be disposed in the other end 1b of the detection device main body 1, but it is preferable that the takeout terminal (the takeout terminal 12a) of one of the electrodes (the electrode 12) is disposed in the other end 1b of the detection device main body 1 and that the takeout terminal (the takeout terminal 11a) of the other electrode (the electrode 11) is disposed at a position between the one end 1a and the other end 1b of the detection device main body 1. In consequence, the takeout terminal (the takeout terminal 12a) of the one electrode (the electrode 12) and the takeout terminal (the takeout terminal 11a) of the other electrode (the electrode 11) are arranged with a space therebetween, whereby when the voltage is applied across the takeout terminal 11a and the takeout terminal 12a to apply the voltage across the pair of electrodes 11, 12, surface creepage can be prevented from being caused in the surface of the detection device main body 1. Here, "the one end of the detection device main body" mentioned in the present embodiment is a region from one tip portion 1c of the detection device main body to a position corresponding to a length of 30% of the whole length of the detection device main body 1. Moreover, "the other end of the detection device main body" mentioned herein is a region from the other tip portion 1d of the detection device main body to a position corresponding to a length of 30% of the whole length of the detection device main body 1. Therefore, a position between the one end 1a and the other end 1b of the detection device main body 1 is a portion obtained by excluding the regions of the one end 1a and the other end 1b from the detection device main body 1. In the particulate matter detection device 100 of the present embodiment, a distance between the takeout terminal 11a and the takeout terminal 12a is preferably 5 to 100 mm, further preferably 10 to 70 mm. When the distance is shorter than 5 mm, a short-circuit is easily caused by the surface creepage at times. In a case where the distance is longer than 100 mm, when the detection device main body 1 of the particulate matter detection device 100 is attached to the pipe or the like so as to position the takeout terminal 11a outside the pipe, the portion of the detection device main body 1 protruding externally from the pipe becomes excessively long, and it becomes difficult to mount the detection device main body 1 in a small space at times.

Moreover, a distance between the through hole 2 and the takeout terminal 11a disposed at the position between the one end 1a and the other end 1b of the detection device main body 1 is preferably 10 mm or more, further preferably 20 mm or more. In a case where the distance is shorter than 10 mm, when the particulate matter detection device 100 is attached to the pipe so as to insert the portion of the through hole 2 into the pipe, the heat of the high-temperature exhaust gas circulating through the pipe easily exerts an influence on the takeout terminal 11a on occasion.

There is not any special restriction on the shape and size of the takeout terminal 11a. The takeout terminal preferably has a polygonal shape such as a quadrangular shape having a width of 0.5 to 3 mm and a length of 0.5 to 3 mm, but may have another shape such as a circular shape, an elliptic shape or a race track-like shape. Examples of the material of the takeout terminal 11a include Ni, Pt, Cr, W, Mo, Al, Au, Ag, Cu, stainless steel, and Kovar.

As an example of a method of detecting the mass of the particulate matter, there is a method of measuring the changes of the electric properties of the pair of electrodes 11, 12 caused by adsorbing the charged particulate matter by the electrodes. In a specific example of the method, for example, an impedance calculated from a static capacity across the pair of electrodes 11, 12 is measured, and the mass of the adsorbed particulate matter is calculated from the change of the impedance to detect (the mass of) the particulate matter in the exhaust gas. Therefore, the particulate matter detection device 100 of the present embodiment preferably further includes a measurement section connected to the takeout terminals 11a, 12a to measure the impedance across the electrodes 11, 12. Examples of the measurement section include an LCR meter and an impedance analyzer or the like capable of measuring not only the static capacity but also the impedance.

In the particulate matter detection device 100 of the present embodiment, the detection device main body 1 is formed so as to be prolonged in one direction, and there is not any special restriction on the length of the main body in the longitudinal direction thereof, but the length is preferably a length capable of efficiently sampling the particulate matter in the exhaust gas when inserted into the exhaust gas pipe. In the particulate matter detection device 100 of the present embodiment, the through hole 2 is formed in the one end 1a of the main body in the longitudinal direction thereof. Moreover, there is not any special restriction on the thickness of the detection device main body 1 (the length of the main body in a direction (a thickness direction) vertical to both "the longitudinal direction of the detection device main body" and "a gas circulating direction"), but the main body preferably has a length of, for example, about 0.5 to 3 mm. Here, "the thickness of the detection device main body 1" is the thickness of the thickest portion of the main body in the thickness direction thereof. Moreover, there is not any special restriction on the length of the detection device main body 1 in the circulating direction of the gas circulating through the through hole 2 (the length of the main body in the gas circulating direction), but the main body preferably has a length of, for example, about 2 to 20 mm. Furthermore, the length of the detection device main body 1 in the longitudinal direction thereof is preferably 10 to 100 times the thickness of the detection device main body 1, and preferably 3 to 100 times the length of the detection device main body 1 in the gas circulating direction. As shown in FIGS. 1A and 1B, the detection device main body 1 may have a plate-like shape with a rectangular sectional shape crossing the longitudinal direction thereof at right angles, a rod-like shape with a circular or elliptic sectional shape or the like, or another shape as long as the shape is prolonged in one direction. The material of the detection device main body 1 is preferably at least one selected from the group consisting of alumina, cordierite, mullite, glass, zirconia, magnesia, and titania. Moreover, cordierite is further preferable, because it has an excellent resistance to heat shock. These materials are all dielectric materials, and hence when the electrodes 11, 12 are embedded in the detection device main body 1, the electrodes 11, 12 covered with the dielectric material can be formed. Furthermore, the particulate matter detection device 100 has excellent resistances to heat, dielectric breakdown and the like. Here, "the dielectric material" mentioned in the present embodiment is a substance which is more excellent in dielectric property than in conductivity and which behaves as an insulator against a direct-current voltage.

As shown in FIG. 2, in the particulate matter detection device 100 of the present embodiment, the pair of electrodes 11, 12 are embedded in the wall through which the through hole 2 is formed, and the electrodes 11, 12 covered with the dielectric material are arranged so as to sandwich the through hole 2 therebetween. In consequence, the predetermined voltage can be applied across the electrodes 11, 12 to cause the electric discharge in the through hole 2. It is to be noted that at least a pair of electrodes need to be arranged, and two or more pairs may be arranged. Moreover, the electrodes may only need to be embedded in the wall through which the through hole 2 is formed, and are preferably arranged so as to sandwich the through hole 2 therebetween as shown in FIG. 2. However, the pair of electrodes may be arranged at any position in the wall which surround the through hole 2, as long as the electric properties of the wall can be detected and the electric discharge can be caused in the through hole 2. Moreover, a plurality of pairs of electrodes may be arranged so that the electric discharge and the detection of the electric properties are separately performed by the different pairs of electrodes. The type of the electric discharge is preferably one type selected from the group consisting of silent discharge, streamer discharge, and corona discharge. To cause such electric discharge, the particulate matter detection device 100 of the present embodiment preferably further includes a power source for the electric discharge which is connected to the takeout terminals 11a, 12a. As the power source for the electric discharge, an alternate-current power source, a direct-current power source or the like for a high voltage is preferable. Moreover, as the voltage to be applied for causing the electric discharge, a voltage such as a pulse voltage or an alternate-current voltage of a rectangular wave is preferable. Furthermore, the conditions of the voltage to be applied vary with a gap or a gas temperature, but the voltage is preferably 50 to 200 kV/cm. In addition, when the voltage is applied, a power is preferably 0.1 to 10 W.

In the particulate matter detection device 100 of the present embodiment, when the particulate matter contained in the fluid flowing into the through hole 2 is not charged, the electric discharge is caused in the through hole 2 to charge the particulate matter, and the charged particulate matter is electrically adsorbed on the wall surface of the through hole 2. Moreover, when the particulate matter contained in the fluid flowing into the through hole 2 has already been charged before flowing into the through hole 2, the particulate matter does not have to be charged anew by the electric discharge in the through hole 2, so that the electric discharge is not caused in the through hole 2 but the charged particulate matter is electrically adsorbed on the wall surface of the through hole 2. When the electric discharge is caused in the through hole 2 to charge the particulate matter, during the electric discharge, the charged particulate matter is electrically attracted toward the electrode having a polarity opposite to that of the charged particulate matter, and is adsorbed on the wall surface. On the other hand, when the particulate matter has been charged before flowing into the through hole 2, the voltage having predetermined conditions is applied across the electrodes 11, 12 to electrically attract the charged particulate matter toward the electrode having the polarity opposite to that of the charged particulate matter. Here, when the particulate matter has been charged before flowing into the through hole 2, the conditions of the voltage to be applied across the electrodes 11, 12 are preferably 4 to 40 kV/cm.

There is not any special restriction on the shapes and sizes of the electrodes 11, 12, as long as the electric discharge can be caused in the through hole 2. Examples of the shape of each electrode include a rectangular shape, a circular shape, and an oblong shape. Moreover, as to the sizes of the electrodes 11, 12, for example, the area of each electrode is preferably 70% or more of that of the through hole 2 seen from the side surface of the main body.

There is not any special restriction on the thicknesses of the electrodes 11, 12, as long as the electric discharge can be caused in the through hole 2. Each electrode preferably has a thickness of, for example, 5 to 30 μm. Examples of the material of the electrodes 11, 12 include Pt, Mo and W.

A distance between one (the electrode 11) of the pair of electrodes and the through hole 2 and a distance between the other electrode (the electrode 12) and the through hole 2 are preferably 50 to 500 μm, further preferably 100 to 300 μm. In such a range, the electric discharge can effectively be caused in the through hole. The distances between the electrodes 11, 12 and the through hole 2 are the thickness of portions of the dielectric materials covering the electrodes 11, 12 facing the through hole 2.

Figure 3:
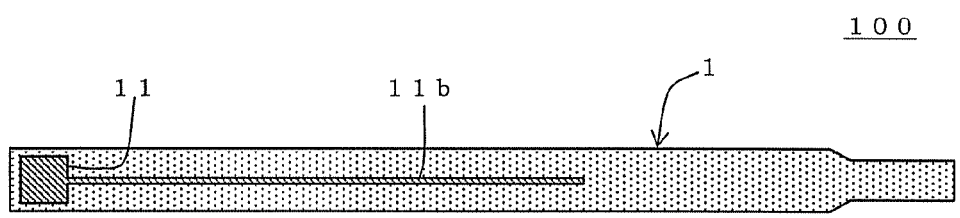
FIG. 3 is a schematic diagram showing a section cut along the B-B' line of FIG. 2.
Figure 4:
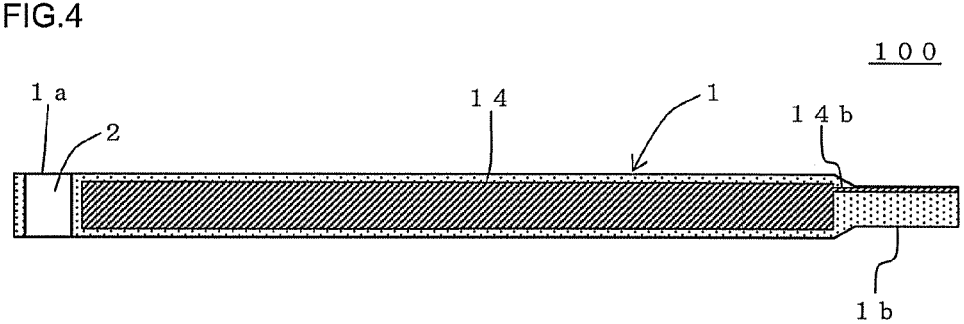
FIG. 4 is a schematic diagram showing a section cut along the C-C' line of FIG. 2.

In the particulate matter detection device 100 of the present embodiment, as shown in FIG. 3, the electrode 11 is connected to a wire 11b extending along the longitudinal direction of the detection device main body 1, and the tip portion of the wire 11b (the tip portion of the wire is not connected to the electrode 11) is interlayer-connected to the takeout terminal 11a shown in FIG. 1B (via-connection). Moreover, as shown in FIG. 4, the through hole 2 is formed in one end 1a of the detection device main body 1. Here, FIG. 3 is a schematic diagram showing a section cut along the B-B' line of FIG. 2, and FIG. 4 is a schematic diagram showing a section cut along the C-C' line of FIG. 2.

Figure 5:
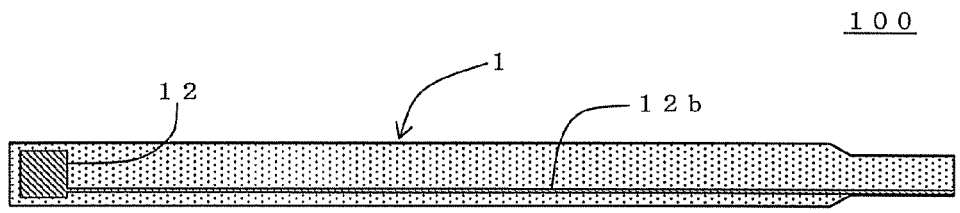
FIG. 5 is a schematic diagram showing a section cut along the D-D' line of FIG. 2.

Moreover, as shown in FIG. 5, the electrode 12 is connected to a wire 12b extending along the longitudinal direction of the detection device main body 1, and the wire 12b is interlayer-connected to the takeout terminal 12a shown in FIG. 1B. Here, FIG. 5 is a schematic diagram showing a section cut along the D-D' line of FIG. 2.

There is not any special restriction on the widths of the wires 11b and 12b, but each wire preferably has a width of, for example, about 0.2 to 1 mm. There is not any special restriction on the thicknesses of the wires 11b and 12b, but each wire preferably has a thickness of, for example, about 5 to 30 µm. Moreover, examples of the material of the wires 11b and 12b include Pt, Mo and W.

As shown in FIGS. 2 to 5, in the particulate matter detection device 100 of the present embodiment, a strip-like ground electrode 14 is disposed at a position sandwiched between the wire 11b and the wire 12b extending from the pair of electrodes 11, 12, respectively. A region provided with the ground electrode 14 is preferably a region capable of disturbing a current flowing from one wire (e.g., the wire 11b) to the other wire (e.g., the wire 12b). Moreover, when the one wire, at lease, is moved in a direction vertical to the ground electrode 14 and superimposed on the ground electrode 14, a portion of the wire having a length of 95% or more of the whole length thereof is preferably superimposed on the ground electrode 14. Furthermore, the ground electrode 14 is preferably disposed in a plane parallel to both the longitudinal direction and the width direction of the detection device main body 1. In addition, preferably, the width of the ground electrode 14 is 70 to 95% of that of the detection device main body 1, and the length of the ground electrode 14 is 50 to 95% of that of the detection device main body 1. Further preferably, the width of the ground electrode 14 is 80 to 90% of that of the detection device main body 1, and the length of the ground electrode 14 is 70 to 90% of that of the detection device main body 1. In consequence, the current flowing from the one wire to the other wire can further effectively be disturbed. Here, "the width of the ground electrode 14" is the length of the ground electrode 14 in the extending direction of the through hole 2 (the circulating direction of the fluid), and "the width of the detection device main body 1" is the length of the detection device main body 1 in the extending direction of the through hole 2 (the circulating direction of the fluid). Moreover, as shown in FIG. 4, the through hole 2 is formed in the one end 1a of the detection device main body 1, and the strip-like ground electrode 14 extending from the through hole 2 to the other end 1b is embedded in the detection device main body 1. FIG. 4 is a schematic diagram showing the section cut along the C-C' line of FIG. 2.

There is not any special restriction on the shape of the ground electrode 14, but examples of the shape include a rectangular shape and an oblong shape. Moreover, there is not any special restriction on the thickness of the ground electrode 14, as long as the current flowing from the one wire to the other wire can be disturbed. The ground electrode preferably has a thickness of, for example, 10 to 200 µm. Examples of the material of the ground electrode 14 include Ni, Pt, Cr, W, Mo, Al, Au, Ag, Cu, stainless steel, and Kovar.

A distance between the ground electrode 14 and the wire 11b and a distance between the ground electrode 14 and the wire 12b are preferably 100 to 500 µm, further preferably 150 to 250 µm, respectively. In such ranges, the current flowing from the one wire to the other wire can effectively be disturbed.

In the particulate matter detection device 100 of the present embodiment, as shown in FIG. 4, the ground electrode 14 is connected to a wire 14b extending along the longitudinal direction of the detection device main body 1, and the tip portion of the wire 14b (the tip portion of the wire is not connected to the ground electrode 14) is interlayer-connected to the takeout terminal 14a shown in FIG. 1B (via-connection).

There is not any special restriction on the width of the wire 14b, but the wire preferably has a width of, for example, about 0.2 to 1 mm. Moreover, there is not any special restriction on the thickness of the wire 14b, but the wire preferably has a thickness of, for example, about 5 to 30 µm. Furthermore, examples of the material of the wire 14b include Pt, Mo and W or the like.

Figure 6:
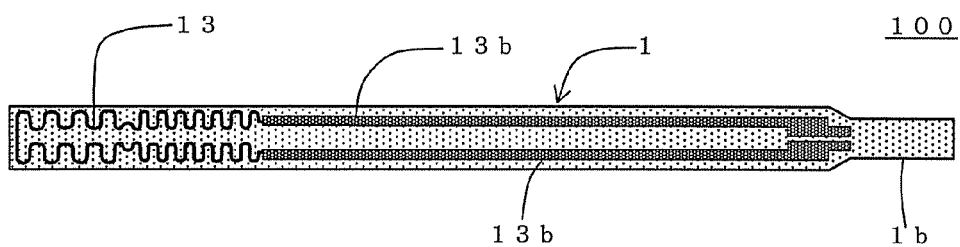
FIG. 6 is a schematic diagram showing a section cut along the E-E' line of FIG. 2.

As shown in FIGS. 2 and 6, the particulate matter detection device 100 of the present embodiment preferably further includes the heating section 13 which is disposed (embedded) in the detection device main body 1 so as to extend along the wall surface of the through hole 2 (the wall surface parallel to the side surface of the detection device main body 1). The heating section 13 can heat and oxidize the particulate matter adsorbed by the electrodes. Moreover, during the measurement of the mass of the particulate matter or the like, the heating section can adjust the internal space of the through hole 2 at a desired temperature, and can control the temperature to stably measure the changes of the electric properties of the wall through which the through hole is formed. The heating section 13 may have a wide film-like shape. Alternatively, as shown in FIG. 6, the heating section may be made of a linear metal material having a wavy shape with a U-turned tip portion. The heating section having such a shape can uniformly heat the inside of the through hole. Examples of the material of the heating section 13 can include Pt, Mo and W. The heating section 13 is preferably embedded in the detection device main body 1 so as to extend along the wall surface of the through hole 2, but the heating section may be formed so as to further extend from the position provided with the through hole 2 shown in FIG. 4 to the other end 1b of the detection device main body 1. In consequence, it is possible to decrease a temperature difference between the inside of the through hole and the vicinity of the through hole, and there is also an advantage that the breakdown of an element does not easily occur even during immediate heating. The heating section 13 can preferably raise the temperature of the internal space of the through hole 2 up to 650° C.

In the particulate matter detection device 100 of the present embodiment, at least one heating section 13 is preferably disposed at a position on the side of at least one of the pair of electrodes 11, 12 opposite to the side thereof provided with the through hole. In the particulate matter detection device 100 of the present embodiment shown in FIG. 2, the heating section 13 is disposed at a position on the side of the electrode 12 opposite to the side thereof provided with the through hole 2. Thus, in a case where the heating section 13 is disposed at the position on the side of at least one of the pair of electrodes 11, 12 opposite to the side thereof provided with the through hole, the changes of the electric properties of the wall through which the through hole 2 is formed are easily measured by the pair of electrodes 11, 12 without being influenced by the heating section 13. In FIG. 2, one heating section 13 is disposed, but a plurality of heating sections may be disposed at positions on the side of the electrode 12 opposite to the side thereof provided with the through hole 2. Moreover, in FIG. 2, the heating section 13 is disposed at the position on the side of one of the pair of electrodes (the electrode 12) opposite to the side thereof provided with the through hole 2, but at least one heating section 13 may preferably be disposed at each position on the side of each of (both of) the pair of electrodes 11, 12 opposite to the side thereof provided with the through hole 2. The arrangement and number of the heating sections 13 may be those necessary for achieving purposes of temperature adjustment, oxidation removal of the collected particulate matter and the like.

As shown in FIG. 6, the heating section 13 is connected to wires 13b, 13b, and the wires 13b, 13b are interlayer-connected to takeout terminals 13a, 13a shown in FIG. 1B, respectively. The takeout terminals 13a of the heating section 13 are preferably disposed in the other end 1b of the detection device main body 1 to avoid the influence of heat exerted when heating the one end 1a side of the detection device main body 1, in the same manner as in the takeout terminals 11a, 12a of the electrodes 11, 12. In FIG. 1B, the takeout terminal 12a is disposed at one edge of the side surface of the detection device main body 1 in the width direction thereof, and the two takeout terminals 13a, 13a and the takeout terminal 12a are arranged side by side, but the arrangement of the takeout terminal 12a and the takeout terminals 13a, 13a is not limited to this arrangement.

When the heating section 13 is linear, there is not any special restriction on the linear width of the heating section, but the section preferably has a width of, for example, about 0.05 to 1 mm. Moreover, there is not any special restriction on the thickness of the heating section 13, but the section preferably has a thickness of, for example, about 5 to 30 μm. There is not any special restriction on the width of the wire 13b, but the wire preferably has a width of, for example, about 0.7 to 4 mm. Moreover, there is not any special restriction on the thickness of the wire 13b, but the wire preferably has a thickness of, for example, about 5 to 30 μm. There is not any special restriction on the width of the takeout terminal 13a for the heating section 13, but the takeout terminal preferably has a width of, for example, about 0.1 to 2 mm. Moreover, there is not any special restriction on the thickness of the takeout terminal 13a, but the takeout terminal preferably has a thickness of, for example, about 5 to 1000 μm. Examples of the material of the wire 13b and the takeout terminal 13a include Ni, Pt, Cr, W, Mo, Al, Au, Ag, Cu, stainless steel, and Kovar.

Moreover, the particulate matter detection device 100 of the present embodiment can preferably apply the voltage across the pair of electrodes 11, 12 and cause the electric discharge in the through hole 2 to oxidize and remove the particulate matter adsorbed by the electrodes. As conditions for causing the electric discharge for oxidizing and removing the particulate matter, an electric field intensity is preferably 10 to 200 kV/cm, and the amount of introduced energy with respect to a substance to be treated is preferably 0.05 to 10 J/μg.

The particulate matter detection device 100 of the present embodiment preferably further includes a power source for heating which is connected to the takeout terminal 13a of the heating section 13. Examples of the power source for heating include a constant-current power source.

Figure 7:
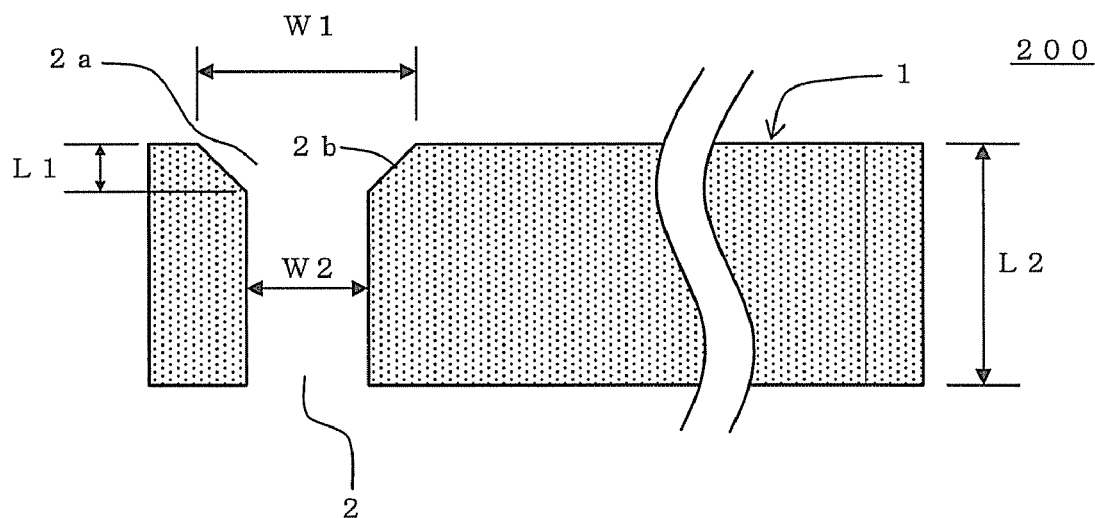
FIG. 7 is a schematic diagram showing another embodiment of the particulate matter detection device of the present invention and corresponding to the schematic diagram of FIG. 4 showing the section of the embodiment of the particulate matter detection device of the present invention.

In the particulate matter detection device 100 of the present embodiment, there is not any special restriction on the shape and size of the through hole 2, as long as the exhaust gas can be passed and the amount of the particulate matter can be measured. The through hole 2 preferably has a length of, for example, about 2 to 20 mm in the longitudinal direction of the detection device main body, and a portion of the through hole 2 sandwiched between the electrodes 11 and 12 preferably has a width of about 3 to 30 mm (the length in a direction vertical to both the longitudinal direction of the detection device main body and the circulating direction of the gas). In such ranges, the exhaust gas including the particulate matter can sufficiently be circulated through the through hole 2, and further the electric discharge effective for charging the particulate matter can be caused in the through hole 2. Moreover, as the shape of the through hole 2, at least one of an inlet portion of the through hole 2 into which the fluid flows and an outlet portion of the through hole from which the fluid is discharged is preferably enlarged. At least one of the inlet portion of the through hole 2 into which the fluid flows and the outlet portion thereof from which the fluid is discharged is enlarged, whereby the exhaust gas or the like to be circulated through the pipe can more efficiently be allowed to flow into (in a case where the inlet portion is enlarged) and/or be discharged from (in a case where the outlet portion is enlarged) the through hole of the particulate matter detection device. In another embodiment (a particulate matter detection device 200) of the particulate matter detection device of the present invention shown in FIG. 7, only an inlet portion 2a of a through hole 2 into which the fluid flows is enlarged to form an enlarged portion 2b. Moreover, in the particulate matter detection device 200 shown in FIG. 7, the through hole 2 is enlarged to expand in the longitudinal direction of a detection device main body 1, but the through hole may be enlarged to expand in the thickness direction of the detection device main body 1. FIG. 7 is a schematic diagram showing the other embodiment of the particulate matter detection device of the present invention and corresponding to the schematic diagram of FIG. 4 showing the section of the embodiment (the particulate matter detection device 100) of the particulate matter detection device of the present invention.

An enlarged width W1 of the enlarged portion 2b (the width of the leading edge portion of the through hole 2 in the gas circulating direction) is preferably 2 to 200% of a width W2 of a portion of the through hole 2 which is not enlarged. Moreover, a depth L1 of the enlarged portion 2b in the gas circulating direction of the through hole 2 (the depth of the enlarged portion) is preferably 5 to 30% of a length L2 of the detection device main body 1 in the gas circulating direction of the through hole 2.

Figure 8A:
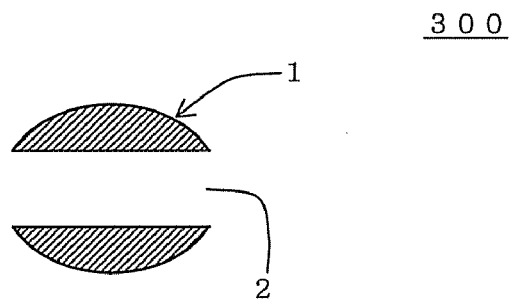
FIG. 8A is a schematic diagram showing a section of still another embodiment of the particulate matter detection device of the present invention crossing the central axis thereof at right angles and including a through hole.
Figure 8B:
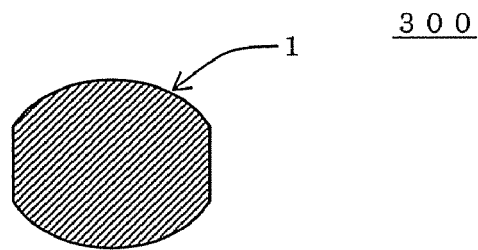
FIG. 8B is a schematic diagram showing a section of a further embodiment of the particulate matter detection device of the present invention crossing the central axis thereof at right angles, and the section does not include any through hole.

As shown in FIGS. 8A and 8B, in still another embodiment (a particulate matter detection device 300) of the particulate matter detection device of the present invention, the sectional shape of a detection device main body 1 crossing the central axis thereof at right angles, preferably gradually thickens from one end of the detection device main body to the center thereof, thickens most at the center thereof, and further gradually becomes thin toward the other end thereof in the extending direction of a through hole 2. When the detection device main body has such a shape and the gas circulating direction of the through hole is aligned (in parallel) with the circulating direction of an exhaust gas in a pipe, the exhaust gas can satisfactorily flow in the pipe. "The center" of the particulate matter detection device (the detection device main body) in the extending direction of the through hole is "a ⅓ region" positioned at the center of the particulate matter detection device when the length of the device in the extending direction of the through hole is divided into three equal lengths. Therefore, "the particulate matter detection device thickens most at the center thereof in the extending direction of the through hole" indicates that the thickest portion of the device is positioned in "the ⅓ region positioned at the center thereof". Here, FIG. 8A is a schematic diagram showing a section of the other embodiment of the particulate matter detection device of the present invention crossing the central axis thereof at right angles and including the through hole, and FIG. 8B is a schematic diagram showing a section of a further embodiment of the particulate matter detection device of the present invention crossing the central axis thereof at right angles, and the section does not include any through hole.

In the detection device main body 1 of the particulate matter detection device 100 of the present embodiment, a plurality of tape-like ceramic materials (ceramic sheets) are preferably laminated. In consequence, the plurality of tape-like ceramic materials can be laminated so as to sandwich electrodes, wires and the like thereamong, thereby preparing the particulate matter detection device 100. Therefore, the particulate matter detection device 100 of the present embodiment can efficiently be manufactured.

The particulate matter detection device 100 of the present embodiment can exert its effect especially when the particulate matter passing through the through hole 2 is soot discharged from a diesel engine.

Next, a method for manufacturing the particulate matter detection device 100 of the present embodiment will be described.

(Preparation of Forming Material)

At least one ceramic material (the dielectric material) selected from the group consisting of alumina, a cordierite forming material, mullite, glass, zirconia, magnesia and titania is mixed with another component used as a forming material to prepare a slurried forming material. As the ceramic material (the dielectric material), the above material is preferable, but the material is not limited to this example. As another material, a binder, a plasticizer, a dispersant, a dispersion medium or the like is preferably used.

There is not any special restriction on the binder, but either an aqueous binder or a nonaqueous binder may be used. As the aqueous binder, methyl cellulose, polyvinyl alcohol, polyethylene oxide or the like can preferably be used. As the nonaqueous binder, polyvinyl butyral, acrylic resin, polyethylene, polypropylene or the like can preferably be used. Examples of the acrylic resin include a (meth)acrylic resin, a (meth)acrylic ester copolymer, and an acrylic ester-methacrylic ester copolymer.

The amount of the binder to be added is preferably 3 to 20 parts by mass, further preferably 6 to 17 parts by mass with respect to 100 parts by mass of the dielectric material. In a case where such an amount of the binder is contained, when the slurried forming material is formed into a green sheet, dried and fired, cracking can be prevented.

As the plasticizer, glycerin, polyethylene glycol, dibutyl phthalate, di-2-ethyl hexyl phthalate, di-isononyl phthalate or the like may be used.

The amount of the plasticizer to be added is preferably 30 to 70 parts by mass, further preferably 45 to 55 parts by mass with respect to 100 parts by mass of the added binder. When the amount is larger than 70 parts by mass, the green sheet becomes excessively soft, and is easily deformed in a step of processing the sheet. When the amount is smaller than 30 parts by mass, the green sheet becomes excessively hard, and cracks when it is only bent, and the handling properties thereof deteriorate at times.

As to the dispersant, anionic surfactant, wax emulsion, pyridine or the like may be used as an aqueous dispersant, or fatty acid, phosphate ester, synthetic surfactant or the like may be used as a nonaqueous dispersant.

The amount of the dispersant is preferably 0.5 to 3 parts by mass, further preferably 1 to 2 parts by mass with respect to 100 parts by mass of the dielectric material. When the amount is smaller than 0.5 part by mass, the dispersibility of the dielectric material lowers, or the green sheet cracks at times. When the amount is larger than 3 parts by mass, the dispersibility of the dielectric material is unchanged, but impurities during firing increase.

As the dispersion medium, water or the like may be used. The amount of the dispersion medium is preferably 50 to 200 parts by mass, further preferably 75 to 150 parts by mass with respect to 100 parts by mass of the dielectric material.

The above materials are sufficiently mixed by using an alumina pot and an alumina ball to prepare the slurried forming material for the preparation of the green sheet. Alternatively, these materials may be mixed by a ball mill of a mono-ball type to prepare the forming material.

Next, the obtained slurried forming material for the preparation of the green sheet is stirred under a reduced pressure, defoamed, and further regulated to obtain a predetermined viscosity. The slurried forming material obtained when preparing the forming material has a viscosity of preferably 2.0 to 6.0 Pa·s, further preferably 3.0 to 5.0 Pa·s, especially preferably 3.5 to 4.5 Pa·s. When the range of the viscosity is regulated in this manner, a slurry can preferably easily be formed into a sheet-like material. When the slurry viscosity becomes excessively high or low, the material is not easily formed at times. It is to be noted that the viscosity of the slurry is a value measured by a B-type viscosity meter.

(Forming Processing)

Next, the slurried forming material obtained by the above method is processed into a tape-like material to form the green sheet which is prolonged in one direction. There is not any special restriction on the forming processing method, as long as the forming material can be processed into the sheet-like material to form the green sheet, but a known method such as a doctor blade method, a press forming method, a rolling method or a calendar roll method may be used. At this time, the green sheets for forming the through hole are prepared so that the through hole is formed when the green sheets are laminated.

The thickness of each green sheet to be manufactured is preferably 50 to 800 μm.

The electrodes, the wires, the heating section and the takeout terminals are arranged on the surfaces of the obtained green sheets. For example, in a case where the particulate matter detection device 100 is prepared as shown in FIGS. 1A, 1B and 2, the electrodes, the wires, the heating section and the takeout terminals are preferably printed at the corresponding positions of the green sheets so as to arrange the electrodes, the wires, the heating section and the takeout terminals at predetermined positions as shown in FIGS. 1B and 4 to 7. A conductive paste for forming the electrodes, the wires, the heating section and the takeout terminals to be arranged is prepared. As to this conductive paste, the binder and a solvent such as terpineol are added to powder which contains at least one selected from the group consisting of gold, silver, platinum, nickel, molybdenum and tungsten in accordance with the materials necessary for forming the electrodes, the wires and the like, respectively, and this powder can sufficiently be kneaded by using a tri-roll mill or the like to prepare the conductive paste. The formed conductive paste containing the materials necessary for forming the electrodes, the wires and the like, respectively, are printed on the surfaces of the green sheets by a screen printing process or the like, to form the electrodes, the wires, the heating section and the takeout terminals having predetermined shapes.

Further specifically, a plurality of green sheets are prepared, and an electrode is provided in one end of one surface of each of the two green sheets, and the wires extending from the electrodes to the other end thereof are provided, to form two green sheets provided with the electrodes. Furthermore, a ground electrode is provided at a position where the one green sheet is superimposed on the wire when the green sheet is superimposed on the green sheets provided with the electrodes, to form the green sheet provided with the ground electrode. Furthermore, a cut portion which becomes the through hole is formed at a position where the one green sheet or the green sheet provided with the ground electrode is superimposed on the electrode when the green sheet is superimposed on the green sheets provided with the electrodes, to form the green sheet provided with the cut portion. When the cut portion is formed in the green sheet provided with the ground electrode, the green sheet provided with the ground electrode is identical to the green sheet provided with the cut portion. Moreover, when the cut portion is formed in the green sheet provided with the ground electrode, the cut portion may first be formed, and the ground electrode may then be disposed. Afterward, green sheets which are not provided with any electrode are superimposed on the two green sheets provided with the electrodes, respectively, to form the green sheets in which the electrodes are embedded in a state in which the electrodes and the wires are covered with the green sheets. Next, the plurality of green sheets are laminated so that the green sheet provided with the ground electrode and the green sheet provided with the cut portion are sandwiched between the two green sheets in which the electrodes are embedded, to form a green sheet laminate having a state in which the cut portion is sandwiched between the two electrodes and in which the ground electrode is sandwiched between the two wires. The plurality of green sheets may simultaneously be laminated. Alternatively, after preparing the green sheets in which the electrodes are embedded, the green sheets and the other green sheets may be laminated. The laminating is preferably performed during pressurizing.

According to the method for manufacturing the particulate matter detection device of the present invention, the desired electrodes and the like are provided in the plurality of green sheets, and the green sheets provided with the electrodes and the like are laminated, dried and fired to manufacture the particulate matter detection device, whereby the particulate matter detection device of the present invention can efficiently be manufactured.

(Firing)

The green sheet laminate is dried and fired to obtain the particulate matter detection device. Further specifically, the obtained green sheet laminate is dried at 60 to 150° C., and fired at 1200 to 1600° C. to prepare the particulate matter detection device. When the green sheets contain an organic binder, the green sheets are preferably degreased at 400 to 800° C. before fired.

EXAMPLES

Hereinafter, the present invention will further specifically be described with respect to examples, but the present invention is not limited to these examples.

Example 1

Preparation of Forming Material

Alumina was used as a dielectric material, polyvinyl butyral was used as a binder, di-2-ethyl hexyl phthalate was used as a plasticizer, sorbitan tri-oleate was used as a dispersant, and an organic solvent (xylene:butanol=6:4 (a mass ratio)) was used as a dispersion medium. These materials were placed into an alumina pot, and mixed to prepare a slurried forming material for the preparation of a green sheet. As the amounts of the used materials with respect to 100 parts by mass of alumina, 7 parts by mass of binder, 3.5 parts by mass of plasticizer, 1.5 parts by mass of dispersant, and 100 parts by mass of organic solvent were set.

Next, the obtained slurried forming material for the preparation of the green sheet was stirred under a reduced pressure, defoamed, and regulated to obtain a viscosity of 4 Pa·s. The viscosity of the slurry was measured by a B-type viscosity meter.

(Forming Processing)

Next, the slurried forming material obtained by the above method was processed into a sheet-like material by use of a doctor blade method. At this time, a green sheet provided with a cut portion was also prepared so as to define a through hole when laminating green sheets. The thickness of the green sheet was set to 250 µm.

On the surfaces of the obtained green sheets, electrodes, a ground electrode, a heating section, wires and takeout terminals were formed as shown in FIGS. 1B and 4 to 7. A conductive paste for forming the electrodes, the ground electrode, the wires and the takeout terminals to be arranged was prepared by adding, to platinum powder, 2-ethyl hexanol as a solvent, polyvinyl butyral as a binder, di-2-ethyl hexyl phthalate as a plasticizer, sorbitan tri-oleate as a dispersant, alumina as a co-material with respect to the green sheet and glass frit as a sintering assistant. The materials were sufficiently kneaded by using a stone mill and a tri-roll mill (in terms of mass ratio, platinum:alumina:glass frit:2-ethyl hexanol:polyvinyl butyral:di-2-ethyl hexyl phthalate:sorbitan tri-oleate=80:15:5:50:7:3.5:1). Moreover, a conductive paste for forming the heating section was prepared by adding, to platinum powder, 2-ethyl hexanol as the solvent, polyvinyl butyral as the binder, di-2-ethyl hexyl phthalate as the plasticizer, sorbitan tri-oleate as the dispersant, alumina as the co-material with respect to the green sheet and glass frit as the sintering assistant. These materials were sufficiently kneaded by using the stone mill and the tri-roll mill (in terms of mass ratio, platinum:alumina:glass frit:2-ethyl hexanol:polyvinyl butyral:di-2-ethyl hexyl phthalate:sorbitan tri-oleate=80:15:5:50:7:3.5:1). The conductive pastes formed in this manner were printed on the surfaces of the green sheets by a screen printing process to form the electrodes and the like having predetermined shapes. Specifically, in a plurality of green sheets, the electrode was provided in one end of one surface of each of the two green sheets, and the wires extending from the electrodes to the other end thereof were provided, to form two green sheets provided with the electrodes. Furthermore, a ground electrode was provided at a position where another green sheet was superimposed on the wires when the green sheet was superimposed on the green sheets provided with the electrodes, to form the green sheet provided with the ground electrode. Furthermore, a cut portion which became the through hole was formed at a position where another green sheet was superimposed on the electrode when the green sheet was superimposed on the green sheets provided with the electrodes, to form the green sheet provided with the cut portion. Afterward, a heating section was formed at a position where another green sheet was superimposed on the cut portion which became the through hole when the green sheet was superimposed on the green sheet provided with the cut portion, and a wire extending from the heating section to the other end thereof was provided, to form the green sheet provided with the heating section. Then, green sheets which were not provided with any electrode or the like were superimposed on the two green sheets provided with the electrodes, respectively, to form the green sheets in which the electrodes were embedded in a state in which the electrodes and the wires were covered with the green sheets. Next, the plurality of green sheets were laminated so that the green sheet provided with the ground electrode and the green sheet provided with the cut portion were sandwiched between the two green sheets in which the electrodes were embedded. Furthermore, the green sheets were laminated so that the green sheet provided with the heating section was positioned outside the green sheets in which the electrodes were embedded, to form a green sheet laminate having a state in which the cut portion was sandwiched between the two electrodes and in which the ground electrode was sandwiched between the two wires. The interlayer-connection (the via-connection) of the wires and the takeout terminals corresponding to the wires was performed by a method of embedding the conductive pastes.

The green sheets were pressurized and laminated by using a uniaxial press machine capable of heating the green sheets, to obtain an unfired article of a particulate matter detection device including the green sheet laminate.

(Firing)

The obtained green sheet laminate (the unfired article of the particulate matter detection device) was dried at 120° C. and fired at 1500° C. to prepare the particulate matter detection device. The obtained particulate matter detection device had a rectangular parallelepiped shape with a size of 0.7 cm×0.2 cm×12 cm, and the other end of the shape became thin as shown in FIG. 1B. The thin other end thereof had a width of 4.25 cm and a length of 1.2 cm. The through hole had a rectangular sectional shape with a size of 10 cm×0.5 cm which was vertical to the circulating direction of an exhaust gas.

(Power Source for Electric Discharge)

As power sources for electric discharge, a pulse power source and a DC power source were used, and connected to the takeout terminals of the electrodes.

(Measurement Section)

As a measurement section for measuring an impedance across the electrodes, an impedance analyzer manufactured by Agilent Technologies was used, and connected to the takeout terminals of the electrodes. Moreover, the takeout terminal of the ground electrode was grounded.

(Measurement Method of Particulate Matter)

The obtained particulate matter detection device was installed to an exhaust line of a diesel engine. As the diesel engine, a direct jet diesel engine of 2000 cc displacement was used. On operating conditions including a rotation speed of 1500 rpm, a torque of 24 N·m, an EGR (exhaust gas recirculation) open degree of 50%, an exhaust gas temperature of 200° C. and an air sucking rate of 1.3 m³ (in terms of room temperature)/minute, the exhaust gas was generated. The amount of the particulate matter in the exhaust gas measured by Smoke Meter (manufactured by AVL, trade name: model 4158) was 2.0 mg/m³. The particulate matter was detected as follows. While the exhaust gas was generated from the diesel engine, an initial static capacity (pF) across the pair of electrodes was measured six times for one minute before charging and collecting the particulate matter. Afterward, the particulate matter was charged and collected for one minute. Then, this charging and collecting operation was stopped, and a static capacity (the static capacity across the pair of electrodes after the collection of the particulate matter for one minute) (pF) was measured six times for one minute again. As each of the initial static capacity and the static capacity after the collection of the particulate matter for one minute, an average value of six measurements was obtained. Then, the mass of the collected particulate matter was calculated from a difference between the initial static capacity and the static capacity after the collection of the particulate matter for one minute. The mass of the particulate matter was calculated by using an analytical curve prepared beforehand for the change of the static capacity with respect to the amount of the adsorbed particulate matter. It is to be noted that during this measurement, the particulate matter was not burnt by a heater. When the particulate matter was charged and collected, a voltage to be applied by a high-voltage power source was set to DC 2.0 kV. When the static capacity across the electrodes was measured by the measurement section, a voltage to be applied was set to AC 2 V, and a frequency was set to 10 kHz. The results are shown in Table 1.

TABLE 1

|  | Static capacity value |
| --- | --- |
| Initial | 1.08 pF |
| After one-minute particulate matter collection | 1.75 pF |

From Table 1, a difference of the static capacity (the impedance) between the initially measured static capacity and the static capacity measured after the collection of the particulate matter was clarified. In consequence, it is seen that the increase of the mass of the particulate matter in the exhaust gas can be detected even by the measurement of the impedance for one minute.

The particulate matter detection device of the present invention can preferably be used for immediately detecting the occurrence of the defect of a DPF and recognizing the abnormality of the filter, which can contribute to the prevention of air pollution.

What is claimed is:

1. A particulate matter detection device comprising: a detection device main body which has one end provided with at least one through hole and which is prolonged in one direction; at least a pair of electrodes embedded in a wall through which the through hole is formed, and covered with a dielectric material; wires extending from the pair of electrodes respectively to the other end of the detection device main body; and a strip-like ground electrode provided at a position sandwiched between the wires extending from the pair of electrodes respectively, the particulate matter detection device being configured to electrically adsorb, on the wall surface of the through hole, a charged particulate matter contained in a fluid flowing into the through hole, or a particulate matter which is charged by electric discharge caused in the through hole by applying a voltage across the pair of electrodes and which is contained in the fluid flowing into the through hole, and being configured to measure the changes of the electric properties of the wall through which the through hole is formed, thereby detecting the particulate matter adsorbed on the wall surface of the through hole.

2. The particulate matter detection device according to claim 1, wherein the detection device main body has the other end provided with a takeout terminal of at least one of the pair of electrodes.

3. The particulate matter detection device according to claim 2, wherein the ground electrode is disposed in a plane parallel to both the longitudinal direction and the width direction of the detection device main body, the width of the ground electrode is 70 to 95% of that of the detection device main body, and the length of the ground electrode is 50 to 95% of that of the detection device main body.

4. The particulate matter detection device according to claim 2, further comprising:
a heating section for temperature control provided in the detection device main body so as to extend along the wall surface of the through hole, and configured to stably measure the changes of the electric properties of the wall through which the through hole is formed,
the detection device main body having the other end being provided with a takeout terminal of the heating section.

5. The particulate matter detection device according to claim 2, wherein at least one of an inlet portion of the through hole into which the fluid flows and an outlet portion of the through hole from which the fluid is discharged is enlarged.

6. The particulate matter detection device according to claim 2, wherein the sectional shape of the detection device main body crossing the central axis thereof at right angles gradually thickens from the one end of the detection device main body to the center thereof, thickens most at the center thereof, and further gradually becomes thin toward the other end thereof in the extending direction of the through hole.

7. The particulate matter detection device according to claim 2, which is configured to apply the voltage across the pair of electrodes to cause the electric discharge in the through hole, thereby oxidizing and removing the particulate matter adsorbed on the wall surface of the through hole.

8. The particulate matter detection device according to claim 2, wherein the electric discharge caused in the through hole is one type selected from the group consisting of silent discharge, streamer discharge, and corona discharge.

9. The particulate matter detection device according to claim 2, wherein the dielectric material is at least one selected from the group consisting of alumina, cordierite, mullite, glass, zirconia, magnesia, and titania.

10. The particulate matter detection device according to claim 1, wherein the ground electrode is disposed in a plane parallel to both the longitudinal direction and the width direction of the detection device main body, the width of the ground electrode is 70 to 95% of that of the detection device main body, and the length of the ground electrode is 50 to 95% of that of the detection device main body.

11. The particulate matter detection device according to claim 10, further comprising:
a heating section for temperature control provided in the detection device main body so as to extend along the wall surface of the through hole, and configured to stably measure the changes of the electric properties of the wall through which the through hole is formed,
the detection device main body having the other end being provided with a takeout terminal of the heating section.

12. The particulate matter detection device according to claim 1, further comprising:
a heating section for temperature control provided in the detection device main body so as to extend along the wall surface of the through hole, and configured to stably measure the changes of the electric properties of the wall through which the through hole is formed,
the detection device main body having the other end being provided with a takeout terminal of the heating section.

13. The particulate matter detection device according to claim 1, wherein at least one of an inlet portion of the through hole into which the fluid flows and an outlet portion of the through hole from which the fluid is discharged is enlarged.

14. The particulate matter detection device according to claim 1, wherein the sectional shape of the detection device main body crossing the central axis thereof at right angles gradually thickens from the one end of the detection device main body to the center thereof, thickens most at the center thereof, and further gradually becomes thin toward the other end thereof in the extending direction of the through hole.

15. The particulate matter detection device according to claim 1, which is configured to apply the voltage across the pair of electrodes to cause the electric discharge in the through hole, thereby oxidizing and removing the particulate matter adsorbed on the wall surface of the through hole.

16. The particulate matter detection device according to claim 1, wherein the electric discharge caused in the through hole is one type selected from the group consisting of silent discharge, streamer discharge, and corona discharge.

17. The particulate matter detection device according to claim 1, wherein the dielectric material is at least one selected from the group consisting of alumina, cordierite, mullite, glass, zirconia, magnesia, and titania.

* * * * *